United States Patent
Mullins et al.

(10) Patent No.: US 6,783,273 B1
(45) Date of Patent: Aug. 31, 2004

(54) METHOD FOR TESTING INTEGRITY OF CONCRETE SHAFTS

(75) Inventors: Austin Gray Mullins, Odessa, FL (US); Stanley C. Kranc, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 10/249,508

(22) Filed: Apr. 15, 2003

Related U.S. Application Data

(60) Provisional application No. 60/319,196, filed on Apr. 22, 2002.

(51) Int. Cl.[7] .................... G01N 25/00; G01N 25/72; G01K 3/00
(52) U.S. Cl. ..................... 374/45; 374/4; 374/137; 374/53
(58) Field of Search ................ 374/4, 45, 53, 374/136, 137, 141, 148; 73/803

(56) References Cited

U.S. PATENT DOCUMENTS

| | | |
|---|---|---|
| 2,815,578 A | 12/1957 | Broussard |
| 4,120,166 A | 10/1978 | Brooks, Jr. |
| 4,232,554 A | 11/1980 | Aleck |
| 4,715,726 A * | 12/1987 | Tsuruta ................. 374/102 |
| 4,748,855 A | 6/1988 | Barnoff |
| 4,943,930 A | 7/1990 | Radjy |
| 5,041,987 A | 8/1991 | Kuwahara et al. |
| 5,379,237 A | 1/1995 | Morgan et al. |
| 5,414,648 A | 5/1995 | Morgan et al. |
| 5,616,866 A | 4/1997 | Murakami |
| 5,741,971 A | 4/1998 | Lacy |
| 5,829,920 A | 11/1998 | Christenson |
| 5,992,250 A | 11/1999 | Kluth et al. |
| 2001/0035053 A1 * | 11/2001 | McAfee et al. ........... 73/803 |

* cited by examiner

*Primary Examiner*—Diego Gutierrez
*Assistant Examiner*—Mirellys Jagan
(74) *Attorney, Agent, or Firm*—Ronald E. Smith; Smith & Hopen, P.A.

(57) ABSTRACT

A method for detecting and locating foreign inclusions in a drilled cylindrical shaft includes the steps of positioning at least one logging tube within the drilled shaft in parallel relation to a longitudinal axis of the drilled shaft, providing a temperature sensing means, identifying a plurality of temperature locations along the extent of the logging tube, pouring concrete into the drilled shaft, covering the at least one logging tube and monitoring in real time the temperature at various depths and radial directions within the logging tube during the hydration phase of the concrete curing. Temperature readings that differ from expected readings are deemed positioned in the vicinity of an anomalous inclusion. The range over which these anomalous readings are detected, the magnitude of the variance, and the orientation are used to predict the size and location of anomalies prior to the full curing of the concrete.

9 Claims, 4 Drawing Sheets

METHOD FOR TESTING INTEGRITY OF CONCRETE SHAFTS

CROSS REFERENCE TO RELATED APPLICATION

This application claims benefit of U.S. provisional application Serial No. 60/319,196 filed on Apr. 22, 2002.

BACKGROUND OF INVENTION

1. Field of the Invention

This invention relates, generally, to the art of concrete construction. More particularly, it relates to the testing of drilled shafts for defects.

2. Description of the Prior Art

Drilled shafts are large-diameter, cylindrically-shaped, concrete foundations cast directly into bored excavations having a depth of up to one hundred meters. They may be used as bridge piers or the like. Drilled shafts exhibit immense lateral stiffness and can be deeply embedded in the soil to overcome problems caused by scour (erosion aggravated by increased stream velocities around pier foundations).

However, imperfections in the concrete can greatly diminish the strength of a drilled shaft. Imperfections arise from the formation of foreign inclusions such as clumps of soil or pockets of drilling fluid that displace the concrete during the pouring process.

A typical drilled shaft has an upstanding cylindrical cage formed by steel reinforcing bars (rebars) embedded therein. The concrete radially inwardly of the cage is known as the core and the concrete radially outward of the cage is known as the protective cover. Imperfections in the core are of less concern than imperfections in the protective cover because if the protective cover is free of foreign inclusions, it will not erode under the harsh, aggressive environment of a bridge pier. Imperfections within the core are thus of little consequence. The thickness of the protective cover is directly related to its ability to stop corrosive elements from attacking the reinforcing steel. Further, both the steel and concrete must be present to provide structural integrity. The centrally positioned concrete core provides less lateral structural capacity than the more peripherally positioned concrete protective cover due to the relatively smaller moment of inertia associated with more centrally located areas. Core imperfections are therefore of less concern with regards to both structural capacity and corrosion protection.

However, if imperfections are in the protective cover, then such cover can be eroded away, thereby exposing the rebars. Corrosion then attacks the rebars and the ability of the drilled shaft to resist lateral bending is substantially diminished.

It is therefore important that the concrete used in a drilled shaft be substantially free of imperfections, especially in the protective cover. There are several well-known tests whereby the structural integrity of a drilled shaft can be tested after the concrete has cured, but such tests have the obvious shortcoming of being unavailable until the concrete has cured. If unacceptable imperfections are then detected, corrective action is difficult and expensive.

Another shortcoming of the known tests is that they best detect defects in the core of the drilled shaft. Defects in the protective cover are not reliably detected. Thus, the tests do a good job of detecting insignificant defects, but a poor job of finding critical defects. Specifically, the known tests include cross-hole sonic logging and small strain sonic echo. The equipment used in these tests attempts to locate anomalies in the cross-section of drilled shafts by measuring arrival times of lateral compression waves from between cast-in-place longitudinal pipes (C.S.L.), or from axial compression waves emitted from a small hammer at the shaft top (S.I.T.). Both methods provide useful information, but provide little useful information concerning anomalies positioned radially outwardly of the rebar cage, i.e., in the protective cover where information concerning anomalies is most needed.

The C.S.L. method clearly delineates anomalies that appear between logging tubes but relies upon subsequent arrival times to estimate the condition surrounding the most direct path of the lateral compression waves. S.I.T. methods produce a qualitative estimate of the integrity of the shaft cross-section, but only the depth of the imperfection can be determined from such qualitative information. Thus, the radial position of the imperfection is unknown, thereby making remedial efforts difficult. Again, both the C.S.L. and the S.I.T. methods cannot be performed until after the concrete has cured.

A means for testing the structural integrity of the concrete before it has cured is needed. If such a means could be found, then the detected imperfections could be corrected before the concrete cures. The needed method would not only identify the depth of each imperfection, but its radial location as well. Such information would greatly facilitate remedial efforts.

An ideal method for detecting the presence of anomalies would detect anomalies in the core and in the protective cover of the drilled shaft prior to curing of the concrete.

The ideal method would further provide information as to the location of each anomaly.

However, in view of the prior art considered as a whole at the time the present invention was made, it was not obvious to those of ordinary skill in the art how concrete could be tested for imperfections before it has cured, nor was it obvious how the location of such imperfections could be determined or how imperfections in the core and in the protective cover of a drilled shaft could be detected.

SUMMARY OF INVENTION

The long-standing but heretofore unfulfilled need for a concrete testing method having utility with uncured concrete is now met by a new, useful, and nonobvious method for detecting and locating foreign inclusions in a drilled shaft. At least one logging tube is positioned within a cylindrical drilled shaft in parallel relation to a longitudinal axis of the drilled shaft. Concrete is poured into the drilled shaft, covering the longitudinal extent of the at least one logging tube. The uppermost end of the at least one logging tube is not covered with concrete so that a temperature sensing means may be introduced into the lumen of said at least one logging tube.

The temperature sensing means is positioned within and is adjustable along the length of the at least one logging tube, i.e., the temperature sensing means is adjustable longitudinally within the at least one logging tube. By moving a temperature sensor from one longitudinal position to another, temperatures associated with a plurality of longitudinally spaced apart temperature locations within the at least one logging tube are sensed.

The structure having at least one logging tube includes a structure having a plurality of logging tubes where each logging tube is substantially parallel to a longitudinal axis of the drilled shaft.

Each temperature sensing means is also adapted to sense temperature in a radial direction relative to a longitudinal axis of a logging tube within which the temperature sensing means is positioned.

Accordingly, each temperature sensing location of a plurality of temperature sensing locations is determined by the location of the logging tube, the longitudinal position of the temperature sensing means along the length of the logging tube, and the radial position of the temperature sensing means relative to the longitudinal axis of the logging tube.

The temperature sensed at each of the temperature locations during the hydration phase of the concrete curing is monitored in real time. A temperature profile of the drilled shaft is thus generated, with temperature anomaly (low or high) readings indicating the presence of foreign inclusions. More particularly, a temperature reading that differs from an expected temperature is deemed to indicate the existence of a foreign inclusion. Significantly, the presence of a foreign inclusion is detected prior to full curing of the concrete.

A cylindrical rebar cage is positioned concentrically within the drilled shaft and a plurality of logging tubes are located in predetermined positions within the core or within the protective cover, or both. The spacing and number of logging tubes is selected such that the frequency of tubes provides sufficient information to detect defects within both the core and the protective cover.

An important object of this invention is to provide a concrete testing method having utility with uncured concrete.

Another important object is to provide a method that determines the integrity of concrete in the protective cover of a drilled shaft.

Still another object is to provide a method that closely identifies the location of a foreign inclusion both by its depth from the surface and by its radial position relative to a longitudinal axis of symmetry of a drilled shaft.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF DRAWINGS

For a fuller understanding of the nature and objects of the invention, reference should be made to the following detailed description, taken in connection with the accompanying drawings, in which.

DETAILED DESCRIPTION

Figure 1:
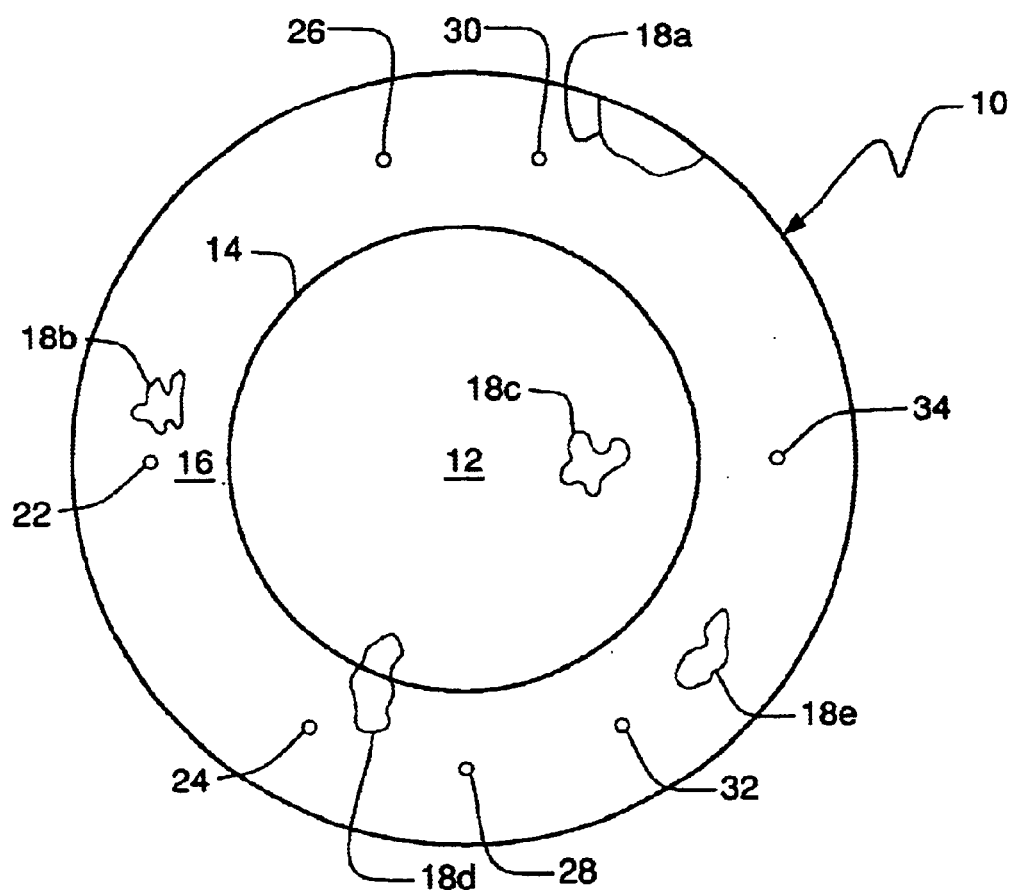
FIG. 1 is a top plan view of a drilled shaft where the logging tubes are located in the cover of the drilled shaft.
Figure 2:
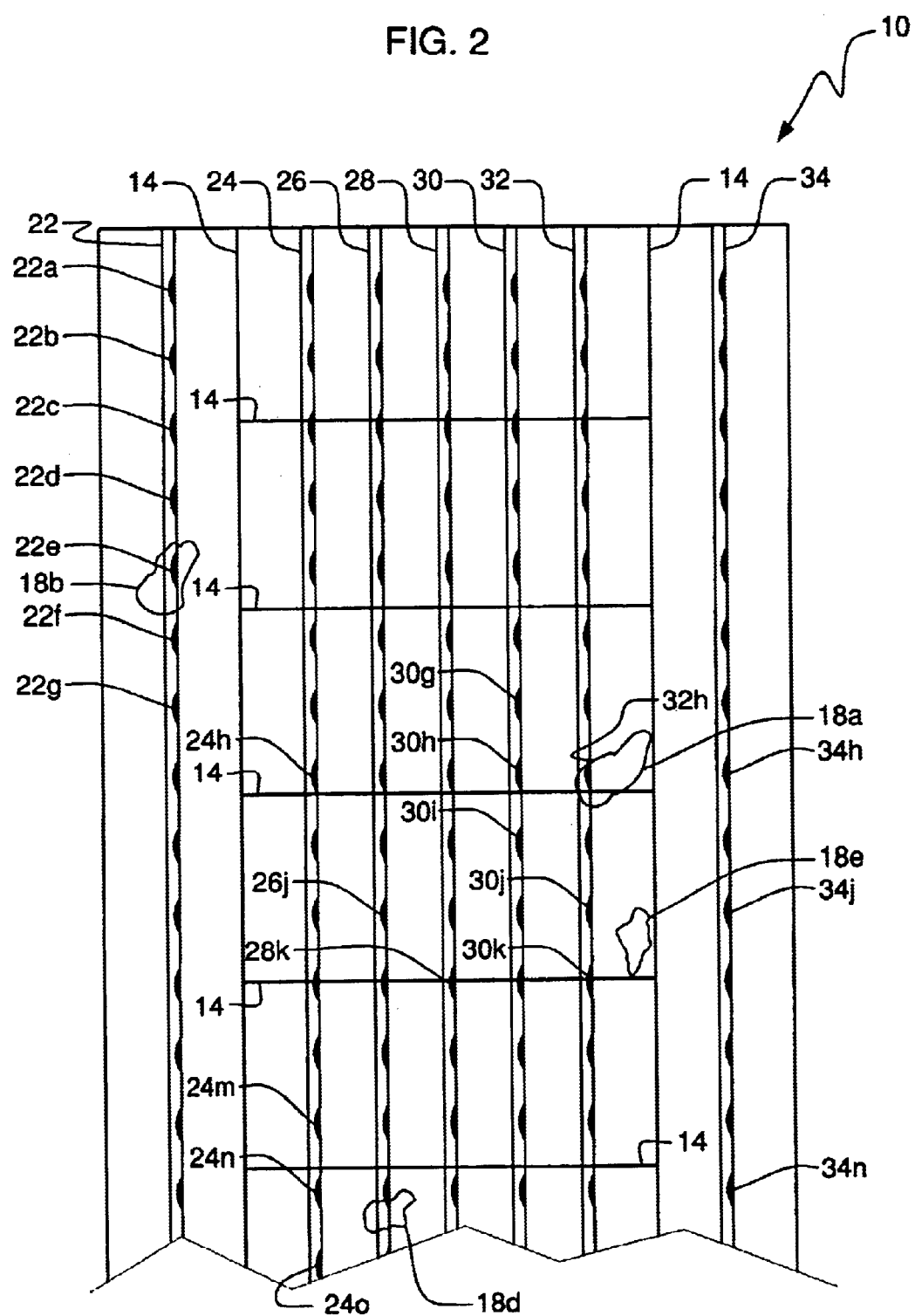
FIG. 2 is a side elevational view of the drilled shaft of FIG. 1.

Referring now to FIGS. 1 and 2, it will there be seen that the reference numeral 10 denotes an illustrative embodiment of the present invention as a whole.

The core of drilled shaft 10 is denoted 12, the rebar cage is denoted 14, and the protective cover is denoted 16. A plurality of foreign inclusions are denoted 18a, 18b, 18c, 18d, and 18e.

Figure 3:
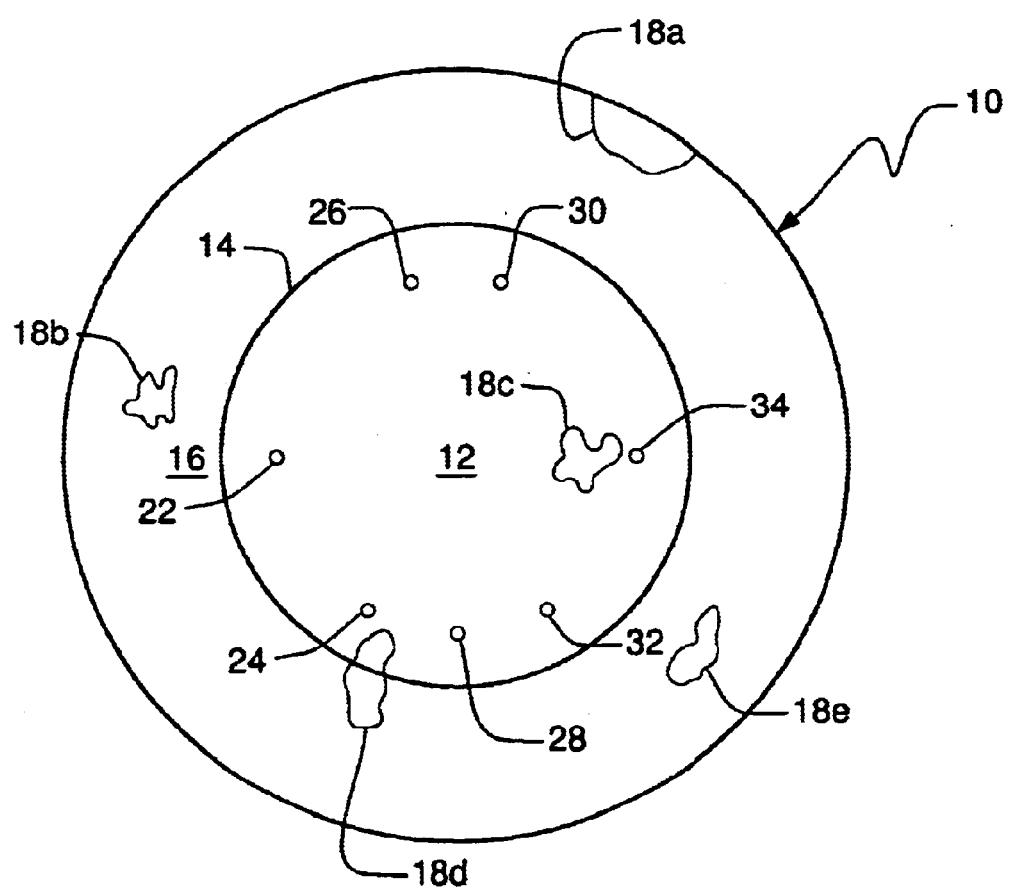
FIG. 3 is a top plan view of a drilled shaft where the logging rubes are located in the core of a drilled shaft.
Figure 4:
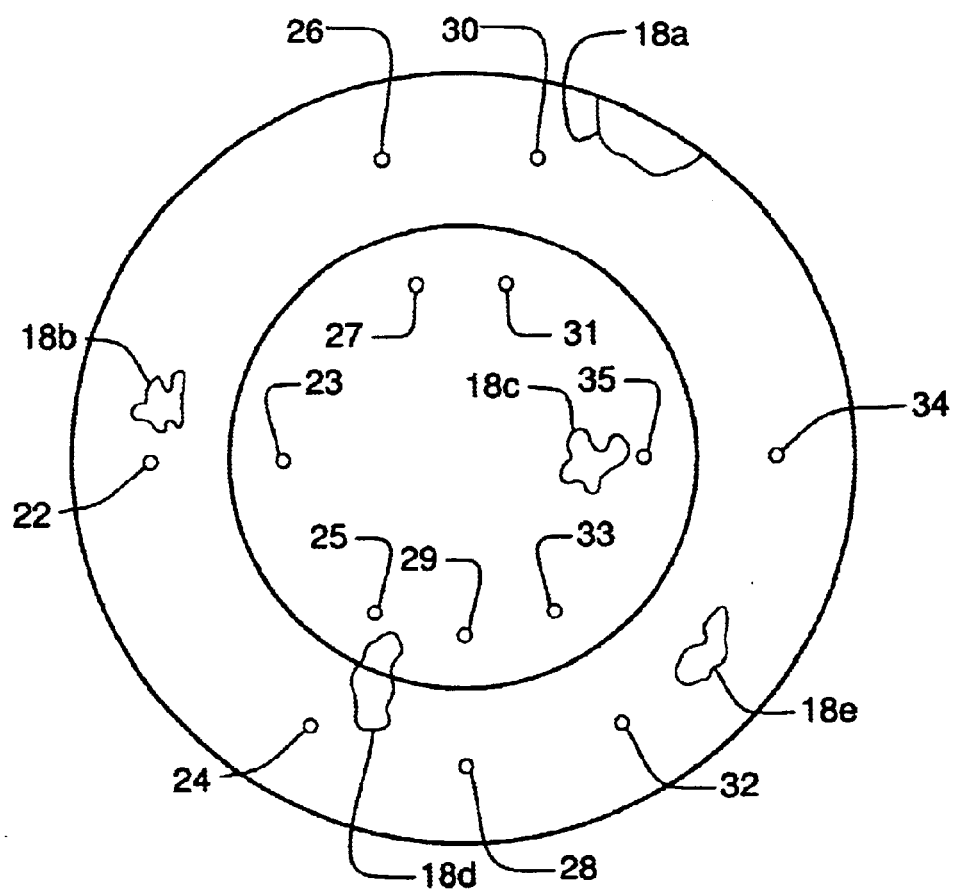
FIG. 4 is a top plan view of a drilled shaft where the logging tubes are located in the cover and in the core of a drilled shaft.

In a first embodiment, depicted in FIGS. 1 and 2, a plurality of logging tubes, denoted 22, 24, 26, 28, 30, 32, and 34 are positioned at preselected locations in the protective cover, i.e., radially outwardly of rebar cage 14 in an upstanding configuration, i.e., in parallel relation to a longitudinal axis of drilled shaft 10. In a second embodiment, depicted in FIG. 3, the logging tubes are positioned radially inwardly of the rebar cage, in the core of the drilled shaft. In a third embodiment, depicted in FIG. 4, the logging tubes are positioned both radially outwardly of the rebar cage and radially inwardly thereof.

The logging tubes are preferably PVC pipes or inclinometer casings cast into the foundation.

A temperature sensing means is provided to establish a first plurality of temperature readings identified by temperature locations denoted 22a, 22b, 22c, etc. positioned at closely spaced intervals along the length of logging tube 22, on the respective interior surfaces thereof. A second plurality of temperature readings is identified by temperature locations denoted 24a, 24b, 24c, etc. positioned at closely spaced intervals along the length of logging tube 24, on the respective interior surfaces thereof, and so on for the remaining logging tubes. In this way, each temperature reading taken by said temperature sensing means is identified by its associated temperature location so that the location is known by the location of the logging tube and the depth at which each reading is taken within the logging tube.

Each logging tube may have a rib or ribs formed in its lumen that prevents rotation of a temperature sensing means. Ribbed logging tubes are not required, however, because other means may be provided for preventing unwanted rotation of a temperature-sensing means. Although one temperature sensing means could be inserted into a logging tube four times to take readings in each of the four major directions, it is more practical to employ a single temperature-sensing probe having four sensors, each circumferentially spaced ninety degrees from its contiguous sensor. This enables the apparatus to sense temperature radially relative to the longitudinal axis of the logging tube so that additional information concerning the temperature profile of the concrete is obtained.

Concrete emits heat during the hydration phase of curing. A foreign inclusion, however, since it lacks concrete, does not cure and thus emits either no heat or substantially less heat than curing concrete. The temperature sensors, accordingly, will detect heat as expected in all areas lacking foreign inclusions, but will detect lower temperatures than expected in areas occupied by such inclusions.

A well-insulated void, however, could produce a rise in temperature due to the insulated volume. No heat is emitted from the void but an elevation in temperature may nonetheless be detected and indicate an imperfection.

In the example given in FIGS. 1 and 2, when the temperature sensing means is positioned at temperature locations 30g, 30h, and 30i, it will detect lower (or possibly higher in the event of an insulated void, as aforesaid) than expected temperatures due to their proximity to foreign inclusion 18a. Temperature readings from locations 22d, 22e, and 22f will indicate lower or higher than expected temperatures due to their proximity to foreign inclusion 18b. In this particular example, a temperature sensor located at temperature location 22e should sense a lower or higher temperature than a temperature sensor located at temperature locations 22d and 22f, thereby further pinpointing the location of foreign inclusion 18b. A temperature sensor located at temperature locations 24n and 24o will detect lower or higher than expected temperatures due to their proximity to foreign inclusion 18d. Temperature sensors located at temperature locations 32j and 32k will detect lower or higher than expected temperatures due to their proximity to foreign inclusion 18e.

Inclusions equidistant from multiple logging tubes are detected similarly by each tube in the radial direction toward the inclusion further identifying the location of the inclusion. Likewise, inclusions between multiple logging tubes, but not necessarily equidistant, are located by the magnitude of temperature variation between adjacent logging tubes.

Foreign inclusions in core 12 are of little concern if protective cover 16 is substantially free of foreign inclusions. However, a drilled shaft having at least one logging tube positioned within the core of the drilled shaft is also within the scope of this invention.

The example of FIGS. 1 and 2 is merely exemplary. The number and positioning of logging tubes throughout drilled shaft 10 may vary widely from the example and may include logging tubes in the core of the drilled shaft as aforesaid. The number of logging tubes, their spacing relative to one another, and the number and positioning of foreign inclusions are all intended merely to convey the concept behind the invention and not to represent any real world application. The logging tubes may also be placed in the materials surrounding curing cement to detect temperature changes in said materials, i.e., the invention is not limited to detecting temperature changes in cement during the hydration phase of concrete curing.

The position of each logging tube is known, and the depth and radial orientation of each sensor when a temperature reading is made is known as well. It follows that information about all detected foreign inclusions is obtained when the temperature sensors generate a real-time temperature profile of drilled shaft 10 during the curing phase. Moreover, the extent over which anomalous temperature measurements are detected provides an indication of the size of each foreign inclusion as well.

When a longitudinal temperature profile has been generated, where defects in the drilled shaft are shown as relatively cool or warm zones of the profile, the results may be compared to computer-generated temperature predictions of a flawless shaft as well as computer-generated temperature predictions of various flawed shaft conditions to provide a probable location and magnitude of the foreign inclusion or inclusions.

Since the novel method provides information about defects before the concrete has cured, it facilitates remedial action such as coring, flushing, and grouting of the affected areas. Such remedial action is most difficult after the concrete has cured.

Preliminary tests on a twenty-four inch (24") diameter shaft, twelve feet (12') in length have been conducted using three (3) logging tubes made of two inch (2") PVC pipes. A seven per cent (7%) cross-sectional inclusion (which percentage is lower than the practical limit of prior art integrity systems of ten per cent (10%) when occurring radially inward of the rebar cage) was easily detected radially outward of the rebar cage, i.e., in the protective zone.

The temperature sensors detect temperature independently of the source of the heat and therefore have utility not just in connection with cement during the hydration phase. Temperature changes in any cementitious material are detectable by using the logging tubes in the way disclosed herein. Moreover, the invention is not limited to applications involving cement or cementitious materials. The temperature of any material that undergoes an exothermic or endothermic reaction can be monitored in accordance with the techniques disclosed herein. A temperature profile can be prepared for structural integrity diagnostic purposes that are not limited to the location of foreign inclusions in curing cement.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

Now that the invention has been described, what is claimed is:

1. A concrete testing method having utility with uncured concrete for detecting and locating foreign inclusions in a drilled shaft, comprising the steps of:
   positioning at least one logging tube within said drilled shaft in parallel relation to a longitudinal axis of the drilled shaft;
   introducing uncured concrete into said shaft in covering relation to exterior sidewalls of said at least one logging tube;
   positioning a temperature sensing means within the lumen of said at least one logging tube before said concrete has cured;
   longitudinally moving said temperature sensing means within said lumen from one position to another along the extent of said at least one logging tube to sense temperatures associated with a plurality of longitudinal positions within the at least one logging tube, and testing the concrete using the sensed temperatures.

2. The method of claim 1, wherein the step of positioning at least one logging tube within said drilled shaft includes the step of positioning a plurality of logging tubes within said drilled shaft in parallel relation to said longitudinal axis of said drilled shaft and wherein the step of longitudinally moving said temperature sensing means from one position to another along the extent of said at least one logging tube includes the step of longitudinally moving said temperature sensing means from one position to another along the extent of each logging tube of said plurality of logging tubes.

3. The method of claim 2, further comprising the steps of:
   concentrically positioning a cylindrical rebar cage within said drilled shaft, thereby defining a core radially inwardly of said cylindrical rebar cage and a protective cover radially outwardly of said cylindrical rebar cage; and
   positioning said plurality of logging tubes in predetermined positions within said core.

4. The method of claim 2, further comprising the steps of:
   concentrically positioning a cylindrical rebar cage within said drilled shaft, thereby defining a core radially inwardly of said cylindrical rebar cage and a protective cover radially outwardly of said cylindrical rebar cage; and
   positioning said plurality of logging tubes in predetermined positions within said protective cover.

5. The method of claim 2, further comprising the steps of:

concentrically positioning a cylindrical rebar cage within said drilled shaft, thereby defining a core radially inwardly of said cylindrical rebar cage and a protective cover radially outwardly of said cylindrical rebar cage; and positioning said plurality of logging tubes in predetermined positions within said core and in predetermined positions within said protective cover.

6. The method of claim 2, further comprising the step of:

radially moving said temperature sensing means from one radial position to another within the lumen of each logging tube of said plurality of logging tubes and sensing a temperature at each of said radial positions whereby the location of each temperature sensing is identified by the location of the logging tube, the longitudinal position of the temperature sensing means within said logging tube, and by the radial position of the temperature sensing means within said logging tube.

7. The method of claim 6, wherein the testing step comprises:

monitoring in real time the temperature sensed at each of said temperature sensing locations during the hydration phase of the concrete curing; and generating a temperature profile of the drilled shaft;

whereby temperature anomaly readings indicate the presence of foreign inclusions; and whereby the presence of a foreign inclusion is detected prior to full curing of the concrete.

8. The method of claim 7, further comprising the steps of:

generating an ideal temperature profile of an ideal drilled shaft having no anomalies; and comparing said ideal temperature profile with said generated temperature profile.

9. The method of claim 7, further comprising the steps of:

preparing a temperature profile of an drilled shaft having known anomalies; and comparing said prepared temperature profile with said generated temperature profile.

* * * * *